(12) United States Patent
Boese et al.

(10) Patent No.: US 7,892,232 B2
(45) Date of Patent: Feb. 22, 2011

(54) MEDICAL TREATMENT DEVICE AND ASSOCIATED METHOD OF OPERATION

(75) Inventors: Jan Boese, Eckental (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 692 days.

(21) Appl. No.: 11/526,177

(22) Filed: Sep. 22, 2006

(65) Prior Publication Data

US 2007/0066899 A1 Mar. 22, 2007

(30) Foreign Application Priority Data

Sep. 22, 2005 (DE) .................. 10 2005 045 363

(51) Int. Cl.
*A61B 18/18* (2006.01)
(52) U.S. Cl. ........................ 606/41; 600/439
(58) Field of Classification Search .................. 606/41; 600/439
See application file for complete search history.

(56) References Cited

U.S. PATENT DOCUMENTS

| | | | |
|---|---|---|---|
| 6,241,725 B1 * | 6/2001 | Cosman | 606/41 |
| 6,259,943 B1 * | 7/2001 | Cosman et al. | 600/429 |
| 6,312,426 B1 * | 11/2001 | Goldberg et al. | 606/33 |
| 6,359,959 B1 * | 3/2002 | Butler et al. | 378/20 |
| 6,383,181 B1 * | 5/2002 | Johnston et al. | 606/24 |
| 6,530,922 B2 * | 3/2003 | Cosman et al. | 606/34 |
| 6,556,695 B1 * | 4/2003 | Packer et al. | 382/128 |
| 6,575,969 B1 * | 6/2003 | Rittman et al. | 606/41 |
| 6,743,226 B2 * | 6/2004 | Cosman et al. | 606/41 |
| 7,275,547 B2 * | 10/2007 | Willis | 128/899 |
| 2002/0111615 A1 * | 8/2002 | Cosman et al. | 606/41 |
| 2004/0138556 A1 * | 7/2004 | Cosman | 600/424 |
| 2005/0192564 A1 * | 9/2005 | Cosman et al. | 606/21 |

FOREIGN PATENT DOCUMENTS

| | | |
|---|---|---|
| DE | 600 10 309 T2 | 7/2002 |
| EP | 0 706 345 B1 | 4/1996 |
| EP | 0 774 232 B1 | 5/1997 |
| WO | WO 01/20552 A1 | 3/2001 |
| WO | WO 01/68173 A2 | 9/2001 |

\* cited by examiner

*Primary Examiner*—Linda C Dvorak
*Assistant Examiner*—Amanda Scott

(57) ABSTRACT

Medical treatment device with an ablation catheter and a visualization device for joint display of the ablation catheter and the anatomy of a part of a patient's body to be treated, whereby the visualization device is embodied for detection of areas of risk of the part of the body to be treated and for displaying the areas of risk jointly with the ablation catheter and the anatomy.

20 Claims, 2 Drawing Sheets

MEDICAL TREATMENT DEVICE AND ASSOCIATED METHOD OF OPERATION

CROSS REFERENCE TO RELATED APPLICATIONS

This application claims priority of German application No. 10 2005 045 363.5 filed Sep. 22, 2005, which is incorporated by reference herein in its entirety.

FIELD OF THE INVENTION

The invention relates to a medical treatment device with an ablation catheter and a visualization device for jointly displaying the ablation catheter and the anatomy of the part of a patient's body to be treated.

BACKGROUND OF THE INVENTION

The use of medical treatment devices in electrophysiological procedures is known. In such cases one or more catheters are introduced for the purpose of electrophysiological mapping or for performing an ablation into anatomical areas of the body of a patient, especially in the heart. An ablation, i.e. a removal of intracardiac tissue, is performed with the aid of an ablation catheter in order to provide permanent therapies for arrhythmias.

However ablation involves a not-insignificant risk for the patient during use close to risky areas, of causing irreparable undesired injuries by the ablation. For treating atrial fibrillation the ablation on the posterior wall of the left atrium can cause a perforation of feed pipes, if the ablation is carried out in the vicinity of the feed pipes against the epicard. Similarly ablation in the vicinity of the pulmonary veins opening out into the left atrium can cause stenoses of the pulmonary veins. Generally ablation in the vicinity of heart valves (mitral valve, tricuspid valve) or in the vicinity of vessel valves (aorta valves, vein valves) can cause valve stenoses or other damage to the valves.

To limit the risk of injuries to the patient as much as possible it is already being proposed that ablation should not be performed exclusively in accordance with electrophysiological criteria, but should also include anatomical criteria. Thus atrial fibrillation is no longer treated by circular lesions around the pulmonary veins in the immediate vicinity of the pulmonary veins, with the risk of causing stenoses of the pulmonary veins, but instead linear lesions are made in the antrum of the left atrium further away from the mouths of the pulmonary veins. Electroanatomical mapping systems are used for this purpose in order to visualize the ablation catheter during the ablation procedure in a representation of the cardiac anatomy.

SUMMARY OF THE INVENTION

The problem underlying the invention is thus that of specifying a medical treatment device with which ablations can be carried out with a reduced risk of injury to the patient.

To resolve this problem there is provision in accordance with the invention, with a medical treatment device of the type mentioned at the start, for the visualization device to be embodied for detection of areas of risk of the part of the body to be treated and for display of the areas of risk jointly with the ablation catheter and the anatomy.

The invention is based on the knowledge that the risk of injuries can be significantly reduced if both the region to be treated, for example a heart chamber, and also anatomical risk areas, for example pulmonary veins, the feed tubes, heart or vessel valves, can be jointly mapped by a visualization device or an electroanatomical mapping system. This produces a real-time visualization of the ablation catheter jointly with the region to be treated and areas of risk. In this way an electrophysiologist is able to see the position of the ablation catheter relative to areas of risk. He can thus carry out the treatment with corresponding care in the vicinity of these areas of risk or he can position the ablation in a less dangerous area. In individual cases he can also decide not to carry out any ablation at all in a risk area.

For the inventive treatment device there can be provision for the visualization device to be embodied for continuous display. Accordingly the ablation catheter, the anatomy of the patient and areas of risk are permanently displayed for the user. This process visualization in real time provides a continuous current image of the area to be treated which reduces the risk of injuries.

It is also within the scope of the invention for the real-time display of the inventive treatment device to be based on intraprocedural 2D imaging or pre-procedural 3D imaging. The use of intraprocedural 3D imaging is preferred however. Where 2D real-time imaging is used, this can be based on intracardiac and/or intraesophageal ultrasound and/or on an x-ray image. Where 3D real-time imaging is used, this can be based on intracardiac ultrasound. Where pre-procedural 3D imaging is used, this can be based on computer tomography examination and/or a magnetic resonance examination and/or an x-ray rotation angiography examination. Pre-procedural 3D imaging is preferably used with relatively movement-invariant structures such as the pulmonary veins for example.

The visualization device of the inventive treatment device can be embodied for carrying out an image registration and/or image diffusion of the display of the ablation catheter and the anatomy of the part of the body to be treated and of the risk areas. This enables both 2D and 3D data to be registered as well as pre-procedural image data with intraprocedural image data.

To guarantee the function of the inventive treatment device it can be embodied for extraction of the areas of risk from the display of the anatomy, with an area of risk preferably being embodied as a point, line, surface or as a volume. The important aspect here is that the extraction of areas of risk is undertaken automatically, so that this is a permanent process not requiring any user input.

In a further embodiment of the invention there can be provision for the treatment device to be embodied for determining a degree of risk with reference to the distance between the extracted area of risk and the ablation catheter. The distance between the ablation catheter and the area of risk is used in this case as a criterion for assessing the danger. A small distance in such cases corresponds to a higher level of danger, conversely a larger distance corresponds to a lower level of danger.

To avoid injury to the patient there can be provision in the inventive treatment device, if a limit value for the degree of danger is exceeded, for a warning signal to be output. The requirement for this is that the degree of danger is calculated continuously in real time, which in its turn requires a continuous recording of the current position of the ablation catheter and of the area or areas of risk. If the limit value is exceeded, a visual and/or audible and/or tactile warning signal can be output. This warning signal allows the user to slow down at the ablation procedure and/or emit less energy to be tissue to be ablated, to break off the procedure entirely or to carry it out at a less dangerous location. Especially preferred is an audible and/or tactile warning signal which can be perceived particularly easily by the user.

In a further embodiment of the invention there can be provision for the intensity of the warning signal to be modified depending on the degree of danger. In this way a progressive warning signal is obtained, in which case, with an audible warning signal for example, the volume increases as the degree of danger becomes greater. In a similar way the tactile feedback can become stronger as the degree of danger increases.

To ensure an especially low-risk treatment there can be provision in the inventive treatment device for the function of the ablation catheter to be influenced depending on the degree of danger. In this case the part of the ablation catheter and/or the duration of its effect and/or the temperature on ablation and can be reduced in particular. If the degree of danger is particularly high the ablation catheter can also be switched off automatically.

In addition the invention relates to a method of operation for a medical treatment device with an ablation catheter and a visualization device for a joint display of the ablation catheter and the anatomy of a part of the body of a patient to be treated.

The inventive method for operation of the medical treatment device comprises the following steps:

Displaying at least one area of risk, calculating the degree of danger, if a threshold value is exceeded for the degree of danger, outputting a warning signal.

BRIEF DESCRIPTION OF THE DRAWINGS

Further advantages and details of the invention will be explained on the basis of an exemplary embodiment which refers to the figures. The figures are schematic diagrams and show.

DETAILED DESCRIPTION OF THE INVENTION

Figure 1:
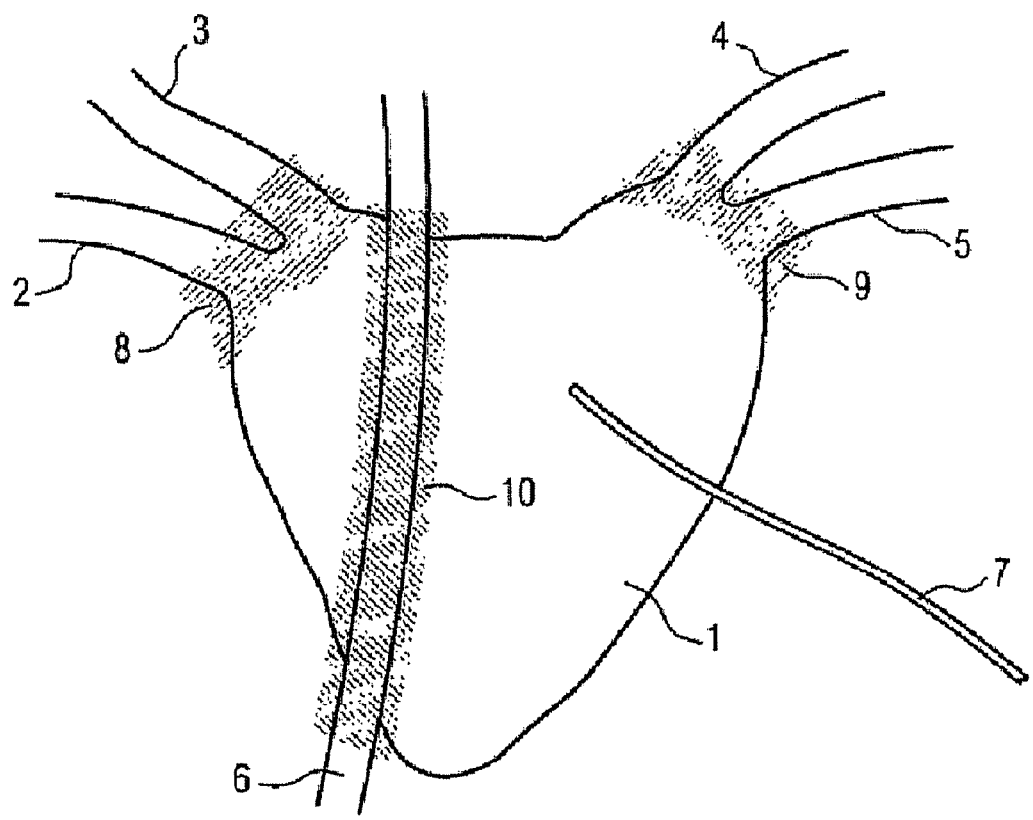
FIG. 1 the joint visualization of ablation catheter, heart chamber and areas of risk during use of the inventive medical treatment device, and FIG. 2 the layout of the inventive medical treatment device.

FIG. 1 shows the joint visualization of ablation catheter, heart chambers and areas of risk when the medical treatment devices are being used.

The diagram shows the left atrium 1 of a patient's heart, pulmonary veins 2 to 5 and the esophagus 6. Likewise an ablation catheter 7 is shown, with which atrial fibrillation can be treated by cauterization of intracardiac tissue.

As shown in FIG. 1, both the region to be treated, namely the heart chamber, and also the anatomical areas at risk, namely the pulmonary veins 2, 3, 4, 5 and the esophagus 6, are mapped by visualization devise 20 to a display or image 21. The esophagus 6 is among the areas of risk for which movement is possibly variable, thus intraprocedural 2D and 3D real-time imaging is used in such cases. To this end and intracardiac ultrasound system (ICE) is used which delivers two-dimensional or three-dimensional images of the left atrium. Optionally the esophagus can also be mapped with the ICE-US system in addition to the cardiac anatomy. In addition a transesophageal echocardiography ultrasound system (TEE) can be used which delivers a corresponding visualization of the esophagus 6. If the intervention concerned only affects the pulmonary veins 2, 3, 4, 5, these could also be mapped with pre-procedural 3D imaging, e.g. with a conventional x-ray system. The process visualization of the esophagus through pre pre-procedural 3D imaging is also possible, if the movement variance of the esophagus is estimated to be insignificant.

A registration and subsequently an image fusion are carried out by the visualization device 20 in order to combine the different image data or representations. This is done using normal registration methods for a 2D-3D or a 3D-3D registration. As shown in FIG. 1, the electrophysiologist can recognize the current position of the ablation catheter 7 relative to potential areas of risk and perform the ablation with the appropriate care in the vicinity of these areas of risk, e.g. by a reduced ablation time or a reduced ablation power. Provided it makes sense in medical terms, the ablation can also be performed at a slightly offset location or not at all.

Areas of risk 8, 9, 10 are extracted by the visualization devise 20 from the recorded image data. An area of risk can be a surface, for example the area of risk in the case of the esophagus 6 can be defined by a surface. With a heart valve the area of risk can be defined by a specific point. In the area of the mouths of the pulmonary veins 2, 3, 4, 5 the area of risk can also be a three-dimensional surface. Areas of risk can also be represented as flat surfaces (e.g. cross section of pulmonary veins) or as lines (e.g. center line of the esophagus).

In the exemplary embodiment shown real-time imaging is used by the visualization device 20 for mapping the areas of risk 8, 9, 10, the extraction of the areas of risk is thus also undertaken by the visualization device 20 continuously during the ablation procedure, meaning that the visualization and the determination of the areas of risk 8, 9, 10 is constantly being updated.

A mapping of the esophagus is achieved by swallowing a stomach probe with a corresponding sensor of the mapping system. The surface or the position of the areas of risk 8, 9, 10 can be identified by this position sensor, the relative position of the area or areas of risk to the position of the ablation catheter 7 can then be determined by the visualization device 20 at the same time. This gives the user a visualization of the anatomy, of the areas of risk 8, 9, 10 and of the ablation catheter 7.

Since the relative position of the ablation catheter 7 to the areas of risk 8, 9, 10 is known, the treatment device can give the user feedback about this spatial relationship. In this case the distance between the current position of the ablation catheter 7 or its tip and the surface or position of an area of risk 8, 9, 10 is determined by the visualization device 20. If this distance falls below a predetermined limit value the ablation catheter 7 can be blocked, meaning that the power can be reduced, alternatively or additionally the temperature can be reduced or the ablation catheter 7 can switched off entirely. The primary aim of this is to give the user a warning, and therefore the blocking of the ablator can be cancelled by active operation of a user interface.

If the distance between the current position of the ablation catheter 7 and the position or the surface of areas of risk 8, 9, 10 falls below a predetermined limit value, a visual, tactile or audible signal is output.

In the medical treatment device different threshold values are provided for different areas of risk, different applications and for the imaging modalities used in each case for mapping the areas of risk. Likewise the limit values can be configured or set differently for different users or user groups.

The visual warning signal can be reproduced at one or more of the medical systems used during the ablation procedure, e.g. at the x-ray system, at an electromagnetic mapping-system or at an electrophysiological recording system.

A tactile warning signal is output if the catheter is being guided with remote navigation, e.g. with a magnetic remote navigation system or a mechanical remote navigation system. In these cases the tactile feedback can be provided to the user via a user interface of the remote navigation system. The user interface can be a joystick or a 6D mouse for guiding the catheter for example.

The warning signals or the power reduction for safety reasons is tailored to the different uses, this feedback or the blocking of the ablation catheter 7 is thus only initiated after a specific power has been output or if the ablation catheter has a specific temperature. Where a limit value for the distance between the position of the ablation catheter 7 and the surface or position of an area of risk 8, 9, 10 is undershot, the duration of the ablation or power output is automatically limited.

Figure 2:
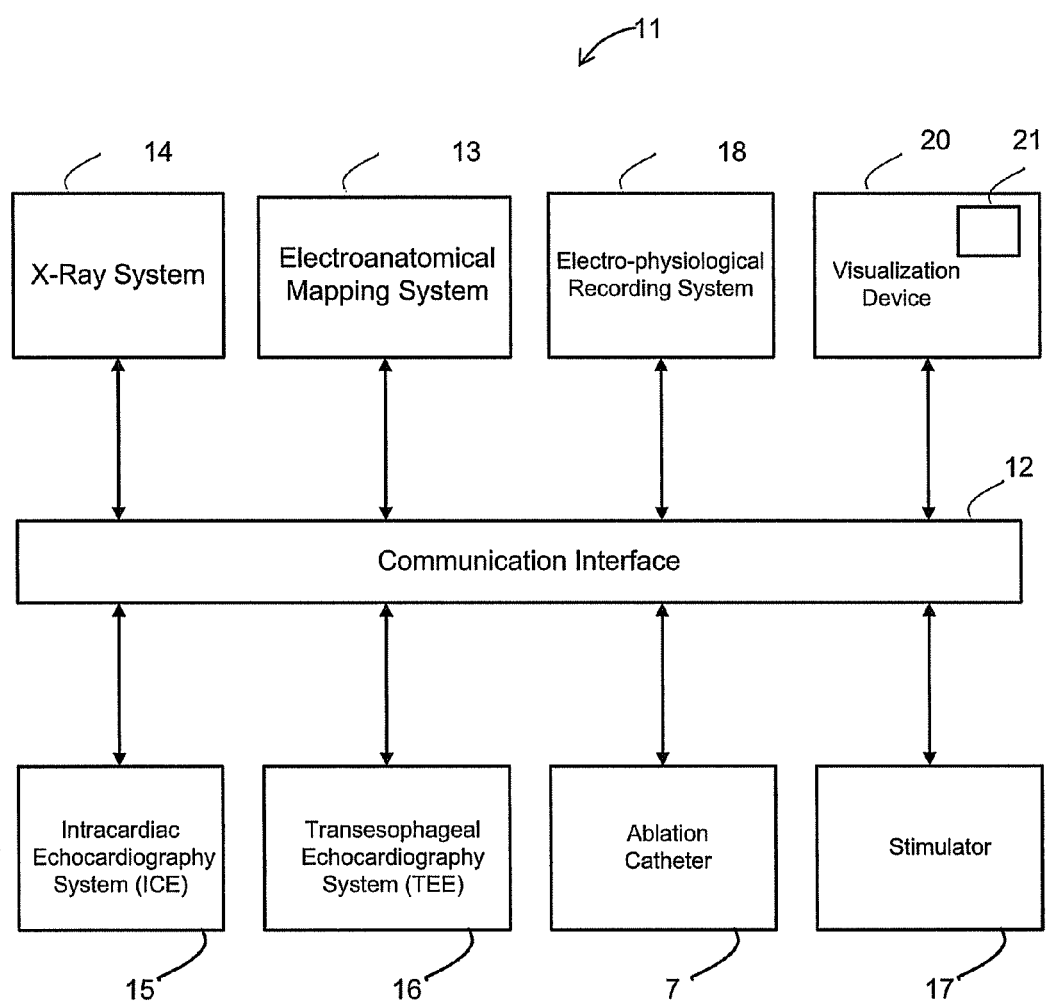

FIG. 2 shows the layout of the medical treatment device.

Since the interaction of different medical engineering systems, devices and components which are used in an electrophysiological procedure is required for the treatment device 11 for imaging, 3D-3D registration, determining distances from areas of risk, the treatment device 11 includes a communication interface 12 embodied as a data bus, via which information is exchanged between the different medical engineering systems, terminals or components involved which are used for electrophysiological ablation procedures. This information or messages is transmitted synchronously or asynchronously and contains status notifications, ECG information 2D or 3D information about anatomical or image-based features determined or position or orientation of instruments, registration information for reconciliation and for registration of device-internal coordinate systems or device-internal configuration information.

To achieve ongoing joint visualization of the heart chamber to be treated, the areas of risk and the position of the ablation catheter 7, an electroanatomical mapping system 13 is provided in the exemplary embodiment shown, in addition 2D real-time imaging is provided. In addition an x-ray system 14 and a intracardiac ultrasound system (ICE) 15 are also used. Furthermore a Transesophageal echocardiography system (TEE) 16 can be connected to the communication interface 12. In addition the ablation catheter 7, a stimulator 17 and an electrophysiological recording system 18 are networked with each other via the communication interface 12.

The treatment device keeps the user informed continuously during an electrophysiological ablation procedure about the distance between the ablation catheter 7 and areas of risk 8, 9, 10. If necessary precautionary measures are taken automatically by the device, which prevent or restrict ablation in the vicinity of areas of risk 8, 9, 10. In this way the risk of injury to the patient in ablation procedures is significantly reduced.

The invention claimed is:

1. A medical treatment device for performing a medical procedure in a patient, comprising:
    an ablation catheter which inserts into a part of a body of the patient to be treated;
    a visualization device which detects a risk area of the part of the body to be treated and displays the risk area jointly with the ablation catheter and an anatomy of the part of the body;
    wherein the risk area is extracted from a display of the anatomy and is displayed as a point, line, flat surface, or a volume;
    a mapping system including a position sensor to measure a position of the risk area and a position of the ablation catheter, to determine a distance between the risk area and the ablation catheter;
    a communication interface configured to exchange information between the ablation catheter, the visualization device and the mapping system;
    wherein a degree of danger is determined based on the distance provided by the mapping system between the extracted risk area and the ablation catheter, said degree of danger being continuously determined in real-time based on the distance between the extracted risk area and the ablation catheter being continuously determined in real-time, said degree of danger being inversely proportional to the distance between the extracted risk area and the ablation catheter;
    and wherein said mapping system is configured to output a warning signal if the degree of danger exceeds a limit value, wherein an intensity of the warning signal is modified depending on the degree of danger.

2. The medical treatment device as claimed in claim 1, wherein the visualization device continuously displays the risk area together with the ablation catheter and the anatomy of the part of the body.

3. The medical treatment device as claimed in claim 2, wherein the visualization device displays the risk area together with the ablation catheter and the anatomy of the part of the body in a real time.

4. The medical treatment device as claimed in claim 3, wherein an intra-procedural 2D imaging is used as a 2D real time imaging for a 2D real time display.

5. The medical treatment device as claimed in claim 4, wherein the 2D real time imaging is selected from the group consisting of: an intracardiac image, an intraesophageal ultrasound image, and an x-ray image.

6. The medical treatment device as claimed in claim 3, wherein an intra-procedural 3D imaging is used as a 3D real time imaging for a 3D real time display.

7. The medical treatment device as claimed in claim 6, wherein the 3D real time imaging is an intracardiac ultrasound image.

8. The medical treatment device as claimed in claim 3, wherein a pre-procedural 3D imaging is used for a 3D real time display.

9. The medical treatment device as claimed in claim 8, wherein the pre-procedural 3D imaging is selected from a group consisting of: a computer topographic image, a magnetic resonance image, and an x-ray rotation angiographic image.

10. The medical treatment device as claimed in claim 1, wherein an image registration of the ablation catheter and the anatomy of the part of the body and the risk areas is performed and the registered image is displayed on the visualization device.

11. The medical treatment device as claimed in claim 1, wherein an image fusion of the ablation catheter and the anatomy of the part of the body and the risk areas is performed and the fused image is displayed on the visualization device.

12. The medical treatment device as claimed in claim 1, wherein the warning signal is selected from the group consisting of: a visual warning signal, an audible warning signal, and a tactile warning signal.

13. The medical treatment device as claimed in claim 1, wherein the ablation catheter is controlled depending on the degree of danger.

14. The medical treatment device as claimed in claim 13, wherein the ablation catheter is controlled by reducing a power or an effective duration or a temperature of the ablation catheter or by switching off the ablation catheter.

15. A method for operating a medical treatment device having an ablation catheter and a visualization device during a medical procedure in a patient, comprising:
    inserting the ablation catheter into a part of a body of the patient to be treated;

displaying the ablation catheter and an anatomy of the part of the body to be treated on the visualization device;

detecting a risk area of the part of the body to be treated from the display;

calculating a degree of danger on a continuous basis in real-time, said calculating based on a distance between the extracted risk area and the ablation catheter;

outputting a warning signal if the degree of danger exceeds a limit value; and modifying an intensity of the warning signal based on the calculated degree of danger.

16. The method of claim 15, further comprising continuous displaying the risk area together with the ablation catheter and the anatomy of the part of the body.

17. The method of claim 16, wherein said continuous displaying occurs in real-time.

18. The method of claim 15, further comprising:
registering an image of the ablation catheter and the anatomy of the part of the body and the risk areas; and
displaying the registered image on the visualization device.

19. The method of claim 15, further comprising:
fusing an image of the ablation catheter and the anatomy of the part of the body and the risk areas; and
displaying the fused image on the visualization device.

20. The method of claim 15, further comprising: selecting the warning signal from the group consisting of a visual warning signal, an audible warning signal and a tactile warning signal.

* * * * *